(12) United States Patent
Kirschman (10) Patent No.: US 8,986,307 B2
(45) Date of Patent: Mar. 24, 2015

(54) SURGICAL INSTRUMENT WITH PIVOTABLE IMPLANT HOLDER

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 126 days.

(21) Appl. No.: 13/545,423

(22) Filed: Jul. 10, 2012

(65) Prior Publication Data

US 2014/0018815 A1    Jan. 16, 2014

(51) Int. Cl.
| A61B 17/70 | (2006.01) |
| A61F 2/44 | (2006.01) |
| A61F 2/46 | (2006.01) |
| A61B 17/88 | (2006.01) |
| A61F 2/30 | (2006.01) |

(52) U.S. Cl.
CPC ........... *A61F 2/4465* (2013.01); *A61B 17/8872* (2013.01); *A61F 2/4611* (2013.01); *A61F 2002/30538* (2013.01); *A61F 2002/30797* (2013.01); *A61F 2002/4623* (2013.01); *A61F 2002/4627* (2013.01); *A61F 2002/4628* (2013.01); *A61F 2002/4629* (2013.01)
USPC .......................................... 606/86 A; 606/99

(58) Field of Classification Search
CPC .................... A61F 2/4611; A61F 2002/30538; A61F 2002/4627; A61F 2002/4628; A61F 2002/4629; A61F 2250/0006
See application file for complete search history.

(56) References Cited

U.S. PATENT DOCUMENTS

| 1,589,508 A | 6/1926 | Boynton |
| 1,607,662 A | 11/1926 | Boynton |
| 1,750,953 A | 3/1930 | Boynton |
| 2,100,319 A | 11/1937 | Brown et al. |
| 2,248,054 A | 7/1941 | Becker |
| 2,877,986 A | 3/1959 | Clavier et al. |
| 3,609,864 A | 10/1971 | Bassett |
| 4,065,941 A | 1/1978 | Aoki |
| 4,463,632 A | 8/1984 | Parke |
| 4,580,563 A | 4/1986 | Gross |
| 4,642,121 A | 2/1987 | Keller |
| 4,716,894 A | 1/1988 | Lazzeri et al. |
| 4,788,976 A | 12/1988 | Dee |
| 4,880,015 A | 11/1989 | Nierman |
| 4,969,888 A | 11/1990 | Scholten et al. |
| 5,098,437 A | 3/1992 | Kashuba et al. |
| 5,100,417 A | 3/1992 | Cerier et al. |
| 5,108,404 A | 4/1992 | Scholten et al. |
| 5,135,528 A | 8/1992 | Winston |
| 5,171,240 A | 12/1992 | Hanwong |
| 5,329,834 A | 7/1994 | Wong |
| 5,372,587 A | 12/1994 | Hammerslag et al. |
| 5,431,671 A | 7/1995 | Nallakrishnan |
| 5,549,637 A | 8/1996 | Crainich |
| 5,667,513 A | 9/1997 | Torrie et al. |

(Continued)

*Primary Examiner* — David Bates
*Assistant Examiner* — Samuel Hanna
(74) *Attorney, Agent, or Firm* — Jacox, Meckstroth & Jenkins (57) ABSTRACT

A surgical instrument for inserting an implant is shown. The instrument has a housing having a first end and a second end, a rotatable drive member having an elongated member comprising a grip that is associated with the first end, an implant holder having a securing member that extends through the second end and that is adapted to receive and hold the implant. A universal joint couples the implant holder and the elongated member and is adapted to permit a user to rotatably drive the implant holder when the implant holder is in a pivoted position.

10 Claims, 9 Drawing Sheets

(56) References Cited

U.S. PATENT DOCUMENTS

| | | | |
|---|---|---|---|
| 5,702,408 | A | 12/1997 | Wales et al. |
| 5,749,878 | A | 5/1998 | Bracy et al. |
| 5,797,918 | A | 8/1998 | McGuire et al. |
| 5,836,958 | A | 11/1998 | Ralph |
| 5,871,204 | A | 2/1999 | Spirer |
| 5,904,689 | A | 5/1999 | Jonjic |
| 5,928,239 | A | 7/1999 | Mirza |
| 6,033,411 | A | 3/2000 | Preissman |
| 6,105,473 | A * | 8/2000 | Huang ............... 81/177.75 |
| 6,174,311 | B1 | 1/2001 | Branch et al. |
| 6,309,403 | B1 | 10/2001 | Minor et al. |
| 6,383,188 | B2 | 5/2002 | Kuslich et al. |
| 6,440,138 | B1 | 8/2002 | Reiley et al. |
| 6,520,967 | B1 | 2/2003 | Cauthen |
| 6,524,238 | B2 | 2/2003 | Velikaris et al. |
| 6,582,432 | B1 | 6/2003 | Michelson |
| 6,599,294 | B2 | 7/2003 | Fuss et al. |
| 6,626,913 | B1 | 9/2003 | McKinnon et al. |
| 6,635,060 | B2 | 10/2003 | Hanson et al. |
| 6,679,886 | B2 | 1/2004 | Weikel et al. |
| 6,755,837 | B2 | 6/2004 | Ebner |
| 6,764,491 | B2 | 7/2004 | Frey et al. |
| 6,830,574 | B2 | 12/2004 | Heckele et al. |
| 6,918,914 | B2 | 7/2005 | Bauer |
| 6,923,814 | B1 | 8/2005 | Hildebrand et al. |
| 7,018,413 | B2 | 3/2006 | Kruger |
| 7,112,206 | B2 | 9/2006 | Michelson |
| 7,235,082 | B2 | 6/2007 | Bartish et al. |
| 7,241,297 | B2 | 7/2007 | Shaolian et al. |
| 7,255,703 | B2 | 8/2007 | Mujwid et al. |
| 7,320,689 | B2 | 1/2008 | Keller |
| 7,473,254 | B2 | 1/2009 | White et al. |
| 7,572,276 | B2 | 8/2009 | Lim et al. |
| 7,575,580 | B2 | 8/2009 | Lim et al. |
| 7,611,515 | B2 | 11/2009 | Wolford et al. |
| 7,708,743 | B2 | 5/2010 | Anderson et al. |
| 7,749,228 | B2 | 7/2010 | Lieberman |
| 7,749,251 | B2 | 7/2010 | Obenchain et al. |
| 7,776,049 | B1 | 8/2010 | Curran et al. |
| 7,828,849 | B2 | 11/2010 | Lim |
| 7,892,239 | B2 | 2/2011 | Warnick et al. |
| 7,892,262 | B2 | 2/2011 | Rhoda et al. |
| 7,901,458 | B2 | 3/2011 | DeRidder et al. |
| 7,905,886 | B1 | 3/2011 | Curran et al. |
| 7,922,719 | B2 | 4/2011 | Ralph et al. |
| 7,959,675 | B2 | 6/2011 | Gately |
| 7,976,549 | B2 | 7/2011 | Dye et al. |
| 7,988,695 | B2 | 8/2011 | Dye |
| 8,097,027 | B2 | 1/2012 | Lim et al. |
| 8,114,092 | B2 | 2/2012 | Altarac et al. |
| 8,118,872 | B2 | 2/2012 | Trudeau et al. |
| D656,610 | S | 3/2012 | Kleiner |
| 8,147,554 | B2 | 4/2012 | Hansell et al. |
| 2001/0021853 | A1 | 9/2001 | Heckele et al. |
| 2001/0034526 | A1 | 10/2001 | Kuslich et al. |
| 2002/0019637 | A1 | 2/2002 | Frey et al. |
| 2002/0032447 | A1 | 3/2002 | Weikel et al. |
| 2003/0208203 | A1 | 11/2003 | Lim et al. |
| 2003/0212402 | A1 | 11/2003 | White et al. |
| 2004/0092933 | A1 | 5/2004 | Shaolian et al. |
| 2004/0153065 | A1 | 8/2004 | Lim |
| 2005/0096745 | A1 | 5/2005 | Andre et al. |
| 2005/0216020 | A1 | 9/2005 | Orton |
| 2006/0189994 | A1 | 8/2006 | Wolford et al. |
| 2006/0229627 | A1 | 10/2006 | Hunt et al. |
| 2006/0235426 | A1 | 10/2006 | Lim et al. |
| 2006/0241761 | A1 | 10/2006 | Gately |
| 2007/0010826 | A1 | 1/2007 | Rhoda et al. |
| 2007/0093850 | A1 | 4/2007 | Harris et al. |
| 2007/0162128 | A1 | 7/2007 | DeRidder et al. |
| 2007/0213737 | A1 | 9/2007 | Schermerhorn et al. |
| 2008/0109005 | A1 | 5/2008 | Trudeau et al. |
| 2008/0140085 | A1 | 6/2008 | Gately et al. |
| 2008/0221694 | A1 * | 9/2008 | Warnick et al. ............. 623/17.16 |
| 2008/0306488 | A1 | 12/2008 | Altarac et al. |
| 2008/0306489 | A1 | 12/2008 | Altarac et al. |
| 2008/0306557 | A1 | 12/2008 | Altarac et al. |
| 2009/0276049 | A1 | 11/2009 | Weiland |
| 2010/0094422 | A1 | 4/2010 | Hansell et al. |
| 2011/0319995 | A1 | 12/2011 | Voellmicke et al. |
| 2012/0130387 | A1 * | 5/2012 | Simpson et al. ............. 606/104 |

\* cited by examiner

FIG. 4 ent after the implant was pivoted to the desired position.
SURGICAL INSTRUMENT WITH PIVOTABLE IMPLANT HOLDER

BACKGROUND OF THE INVENTION

1. Field of the Invention

This invention relates to a surgical implant instrument and system and, more particularly, to an instrument and system having an implant holder having a joint that is adapted to permit the implant holder to be loosened, moved or pivoted to a desired position and tightened before, during and after such movement or pivoting.

2. Background of the Invention

In the past, surgical instruments were provided for applying or inserting implants between adjacent vertebrae in a vertebral column. The implant was positioned or fixed at the end of the instrument usually in a fixed or rigidly connected position.

In some prior art instruments, the tool permitted a variable adjustable alignment of the implant in relation to the instrument. For example, some instruments had a non-pivotable threaded screw that screwed directly into the implant and held the implant in a fixed position at the end of the instrument. In one prior art device, the implant had a pivotable threaded sleeve that permitted the implant to be pivoted relative to an end of the instrument.

In U.S. Pat. No. 6,830,574 B2, another prior art instrument is shown having a holder that is pivotably mounted relative to a shank and is fixable in its position.

One problem with the prior art devices is their complexity and that they either did not permit pivoting of the implant or required multiple components to permit the implant to be pivoted and separate components to fix the implant to the instrument after the implant was pivoted to the desired position.

Another problem with some prior art devices was that the cage implant had to be custom fit to the holder and standard cage implants could not be used. These custom cages oftentimes required an attaching joint that reduced or interfered with the graft space in the case because of the joint in the cage or implant.

What is needed, therefore, is a simplified instrument that is easy to use, improves over the designs of the prior art and/or reduces the number of components necessary to enable a user or surgeon to pivot the implant with respect to the tool and then fix the position of the implant with respect to the tool.

SUMMARY OF THE INVENTION

It is, therefore, an object of one embodiment of the invention to provide a surgical instrument and system that is adapted for fixing to an implant and that permits a loosening of the implant for adjustment, movement or pivoting and then a tightening of the implant on the surgical instrument once the implant is positioned where desired.

Another object of one embodiment of the invention is to provide a surgical instrument and system that utilizes a single device or means for loosening and pivoting the implant and then fixing, locking or clamping the implant to the tool.

Still another object of one embodiment of the invention is to provide a surgical instrument having a universal joint that provides a connector or driving connection that permits the implant holder to be both pivoted and rotated before, during and after pivoting.

Yet another object of one embodiment of the invention is to provide a system having a surgical instrument that is adapted to permit a threaded projection to be secured to an implant, loosened, and pivoted and that is also adapted to rotatably drive the threaded projection prior to, during and after the pivoting of the threaded projection or implant.

Another object of an embodiment of the invention is to provide a surgical instrument having a single rotatable drive member or grip that is adapted to permit both a pivoting of an implant on the instrument and a locking, clamping, securing or fixing of the implant to the surgical instrument after it has been moved or pivoted to a desired position.

Another object of an embodiment of the invention is to provide a universal joint for use in a surgical instrument wherein the universal joint is adapted to permit multiple functions, including pivoting and rotating of an implant holder, to facilitate securing, locking, fixing or clamping of an implant to the instrument.

Another object of another embodiment of the invention is to provide an implant holder that has a pivot joint in the holder and that is adapted to permit a standardized cage to be used.

In one aspect, one embodiment of the invention comprises a surgical instrument for inserting an implant comprising a housing having a first end and a second end, a rotatable member rotatably positioned in the housing, the rotatable member having an elongated member comprising a grip associated with the first end, an implant holder having a securing member that extends through the second end and that is adapted to receive and hold the implant; and a universal joint coupling the implant holder and the elongated member, and the universal joint being situated between the grip and the implant holder, the universal joint being adapted to permit a user to rotatably drive the implant holder when the implant holder is in a pivoted position.

In another aspect, another embodiment of the invention comprises a surgical implant system comprising an implant, a surgical instrument comprising a housing, a drive member rotatably mounted within the housing, an implant holder, a joint rotatably and pivotally coupling the drive member to the implant holder, the joint being adapted to permit a loosing of the implant on the implant holder so that the implant holder may be pivoted or moved to a desired position and being responsive to rotational movement of the drive member to enable said implant to be loosened and pivoted and to cause the implant to become clamped, fixed or locked to the implant holder after the implant holder is pivoted or moved to the desired position.

These and other objects and advantages of the invention will be apparent from the following description, the accompanying drawings and the appended claims.

DETAILED DESCRIPTION OF PREFERRED EMBODIMENTS

Referring now to FIGS. 1-9D, a surgical instrument and system 10 are shown. The surgical instrument and system 10 comprises an implant 12 and a surgical instrument 14 for inserting the implant 12 into a patient. In one illustrative embodiment, the implant 12 is an intervertebral cage and the surgical instrument 14 adapted to insert the intervertebral cage in a disk area (not shown) between a pair of adjacent vertebrae (not shown). In general, one embodiment enables or permits the implant 12 to be mounted on the instrument (e.g., as shown in FIGS. 1A and 1C) and pivoted or moved to a pivoted or desired position (e.g., as shown in FIGS. 1B and 1D). The invention permits loosening and tightening of the implant 12 to the instrument before, during, after and through such pivotal movement.

Figure 2A:
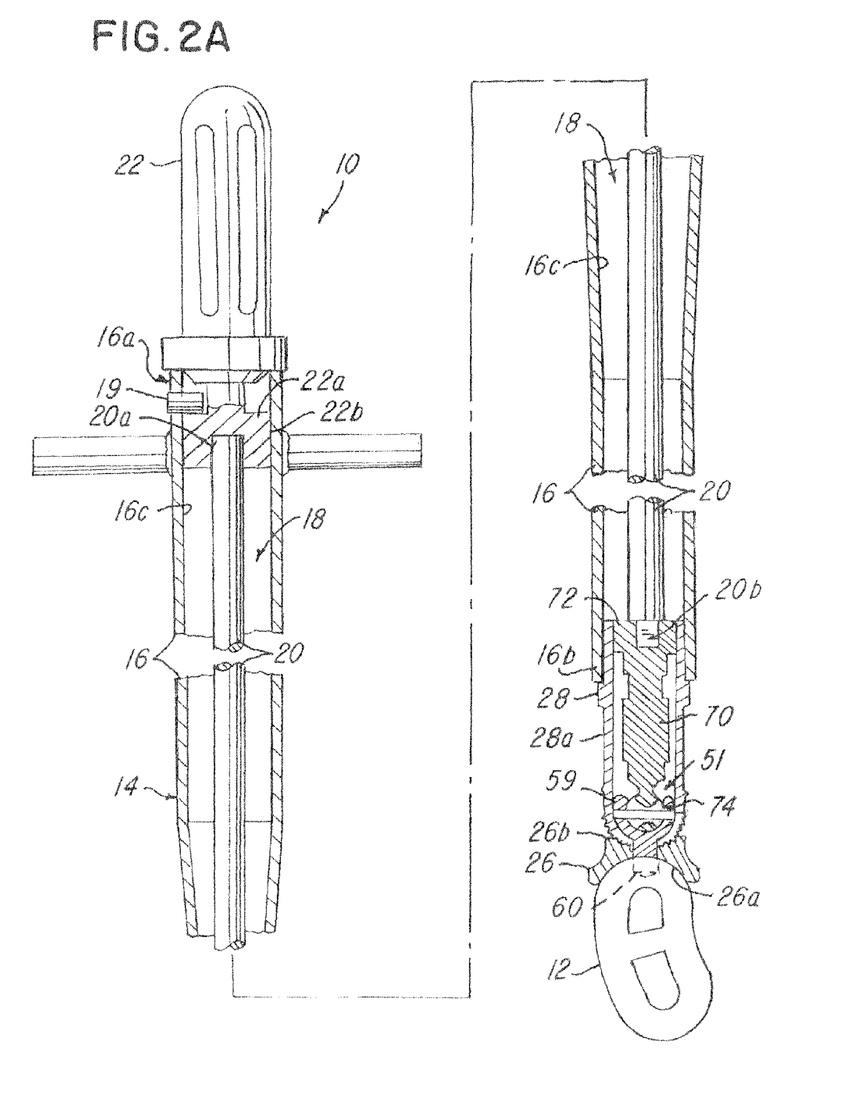
FIGS. 2A and 2B are sectional and exploded views, respectively, of the embodiment shown in FIGS. 1A-1D.
Figure 2B:
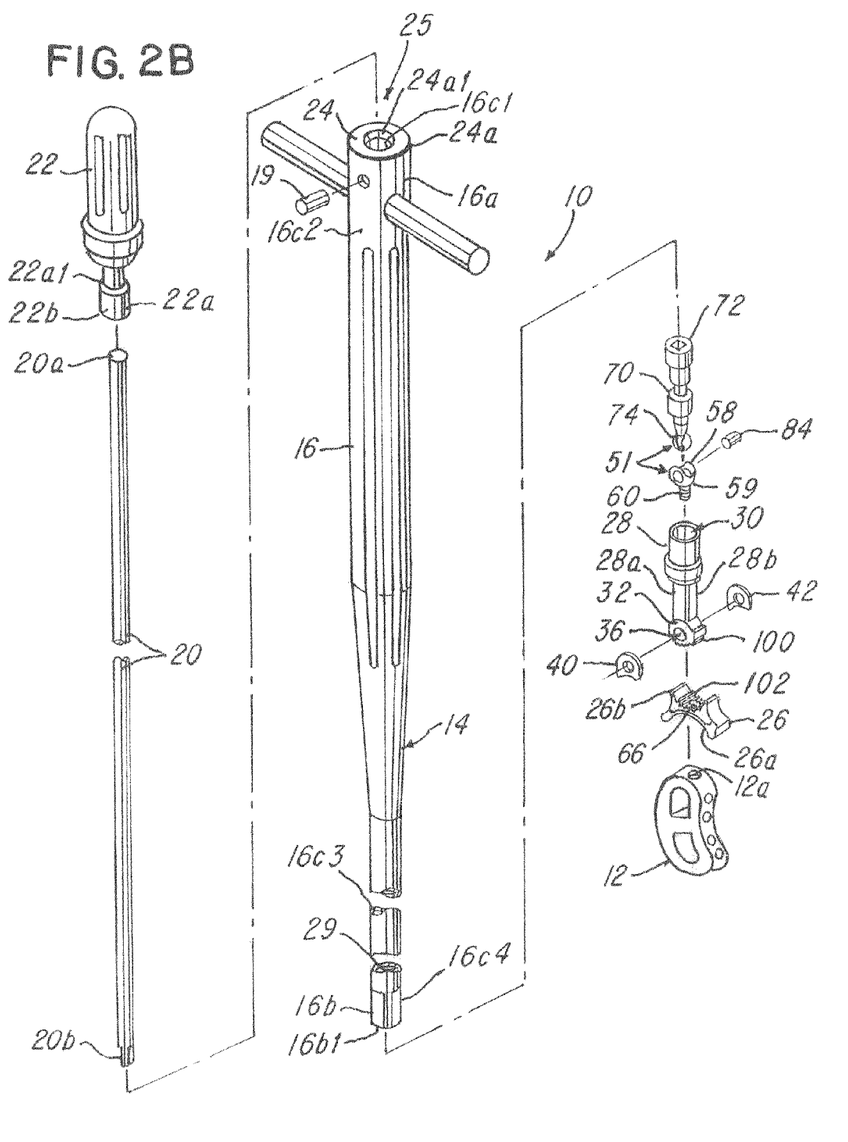

In the illustration being described, the surgical instrument 14 comprises a housing 16 which in one illustrative embodiment is tubular and has a first end 16a and a second end 16b. The housing 16 has an inner wall 16c (FIG. 2A) that defines an interior housing area 18 for receiving a drive member, rotatable member, or rod 20 that is generally elongated and becomes generally aligned with a longitudinal axis A (FIG. 3A) of the surgical instrument 14 when it is received in the housing 16. As shown in FIGS. 2A and 2B, the first end 16a is tubular and has a generally circular inner wall 16c1 and a generally circular outer wall 16c2. The second end 16b is also tubular has a generally circular inner wall 16c3 and a generally square outer wall 16c4.

A first end 16a of the grip 22 comprises a radial cylindrical member or shoulder 22a having an aperture (not shown) for receiving the end 20a of the drive member, rotatable member or rod 20. The end 20a may be secured to the cylindrical member or shoulder 22a of grip 22 by conventional means such as a press fit, weld or adhesive. A set pin 19 (FIGS. 2A and 2B) that prevents the drive member, rotatable member or rod 20 from withdrawing from the housing 16. The cylindrical member or shoulder 22a has a circumference 22b that is dimensioned to provide a bearing surface that cooperates with the inner wall 16c to keep the drive member, rotatable member or rod 20 generally aligned in the housing 16.

FIG. 2A is a sectional view of the instrument 10 and FIG. 2B is an exploded view illustrating various components. The housing 16 comprises the first end 16a having a generally radial wall 24 having an inner wall surface 24a1 that defines an opening 25 that is in communication with the interior housing area 18. The inner wall surface 24a1 provides or defines a shoulder or abutment surface that cooperates with a surface 22a1 of the radial cylindrical member or shoulder 22a to facilitate preventing undesired longitudinal movement of the handle or grip 22 away from the first end 16a and facilitates preventing the drive member, rotatable member or rod 20 from exiting the housing 16.

Figure 1A:
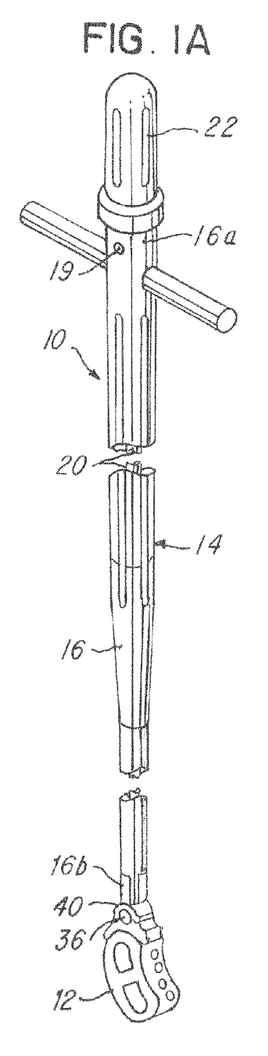
FIGS. 1A-1D are various views of a surgical instrument and system in accordance with one embodiment of the invention.
Figure 1B:
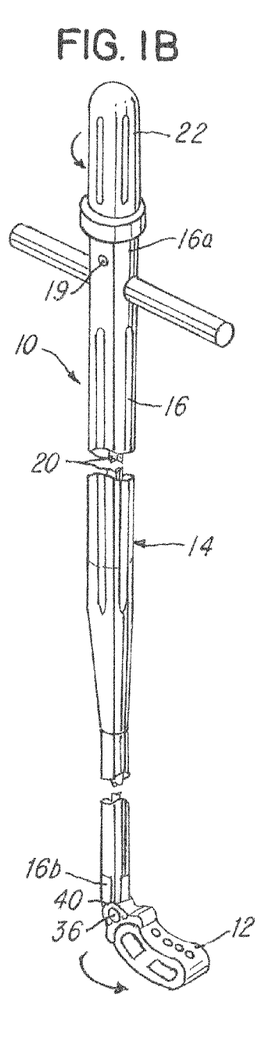
Figure 1C:
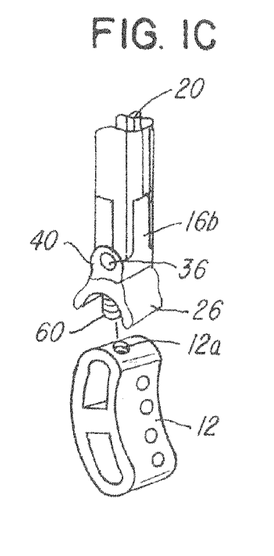
Figure 1D:
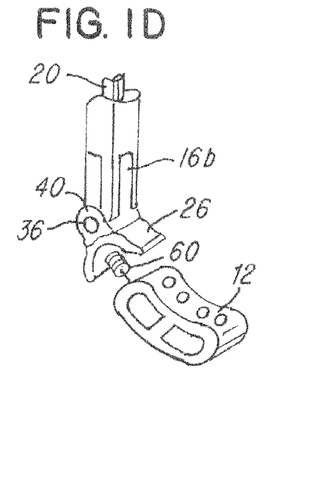

The system or instrument 10 comprises an end assembly 31 (FIG. 5) of components. The end assembly 31 comprises a universal joint 51, an implant holder 58 having a threaded projection 60, a universal joint housing 63 and an abutment member 26 that is pivotally secured to the universal joint housing 63 as described later herein. The universal joint housing 63 has a tubular portion 63a that is received in the end 16b of housing 16 until a surface 63b engages an end 16b(FIG. 1B). A cylindrical bearing sleeve 63c is press-fit into the end 16b during assembly and the end assembly 31 may be welded or secured in the end 16b by conventional means.

In one embodiment, the universal joint 51 comprises a support shaft 70 having an end member 72 (FIG. 5) having an integral cylindrical radial bearing surface 72a that defines or provides a bearing and an aligner for becoming operatively associated with and/or engaging at least a portion of an internal wall 63d of the universal joint housing 63 in order to retain the universal joint housing 63 in a generally centrally located and aligned position within the housing 16.

Figure 3A:
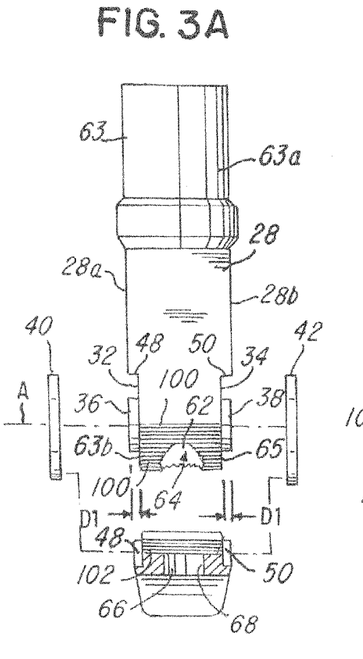
FIG. 3A is a fragmentary and partially exploded view illustrating the device or means for pivotably affixing or securing an abutment member to a housing of the surgical instrument.
Figure 5:
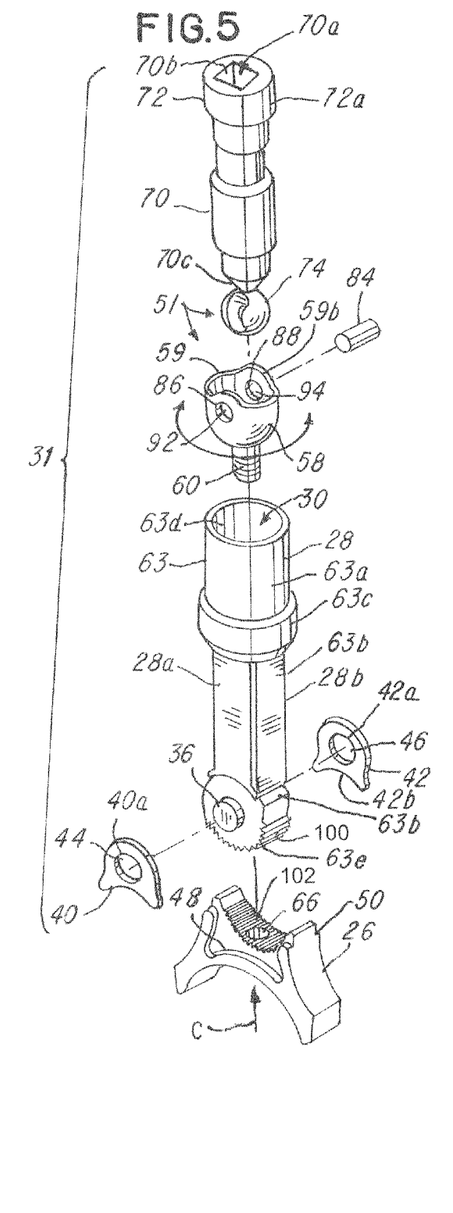
FIG. 5 is an exploded view showing various details of the universal joint used in one embodiment of the invention.

Referring to FIGS. 3A and 5, note that an end 65 of the universal joint housing 63 comprises a tubular wall portion 28 having a first surface or wall 28a and a generally opposing second surface or wall 28b. The first surface 28a and second surface 28b comprise a pair of cut-out areas 32 and 34, respectively. The cut-out areas 32 and 34 are adapted to define or comprise a pair of generally cylindrical projections or pivot pins 36 and 38, respectively. Note that the cylindrical projections or pivot pins 36 and 38 are coaxial along axis A and extend or project from the surfaces or walls 28a and 28b a common distance D1 as shown in FIG. 3A.

The surgical instrument 14 further comprises the abutment member 26 mentioned earlier that is pivotally fixed or secured to the universal joint housing 63. In this regard and as illustrated in FIGS. 3A and 5, the abutment member 26 comprises a pair of flanges 40 and 42. The flanges 40 and 42 comprise generally cylindrical inner walls 40a and 42a which define generally cylindrical openings 44 and 46, respectively. The generally cylindrical openings 44 and 46 receive the projections or pivot pins 36 and 38, respectively, thereby enabling the abutment member 26 to pivot about the axis A (FIG. 5).

The abutment member 26 comprises a pair of generally U-shaped cut-out areas 48 and 50 defined by walls 52 and 54, respectively. The flanges 40 and 42 have generally curved walls 40b (FIG. 5) and 42b respectively, that are complementarily shaped and received in the cut-out areas 48 and 50. The flanges 40 and 42 are then welded, adhered or otherwise secured to the abutment member 26 after the cylindrical openings 44 and 46 are mounted on the projections or pivot pins 36 and 38, thereby pivotally securing and retaining the abutment member 26 to the universal joint housing 63 that is inserted and mounted into the end 16b of housing 16. It should be understood that the inner diameter of the generally cylindrical inner walls 40a and 42a is slightly larger than the outer diameter of the projections or pivot pins 36 and 38 so as to permit some limited "play" and longitudinal movement of the abutment member 26 in the direction of double arrow C (FIG. 5). This feature enables a position of the abutment member 26 to be pivoted or moved about the abutment member axis A and with respect to the second end 16b in a manner described later herein.

Referring back to FIGS. 2A and 2B, the drive member, rotatable member or rod 20 has a second end 20b that is received in an aperture 70a (FIG. 5) defined by wall 70b, thereby providing a connector or coupler for rotatably coupling the grip 22 to the universal joint 51 that is situated in the interior housing area 30.

The surgical instrument 10 further comprises the universal joint 51 which will now be described. The universal joint 51 has an implant holder 58 having the threaded projection 60, as best illustrated in FIGS. 2A-5. An end 63e (FIG. 5) of the universal joint housing 63 comprises an interior slot wall 62 (FIGS. 3A and 3B) that defines a generally arcuate and elongated slot 64 that is in communication with the interior housing area 30 (FIG. 5) mentioned earlier herein. After the abutment member 26 is pivotally secured and mounted to the second end 63e in the manner described earlier, an abutment member aperture 66, which is defined by an abutment member wall 68 (FIG. 3A), becomes aligned with and in communication with the slot 64. When the surgical instrument 10 is assembled, the threaded projection 60 is received in the slot 64 and in abutment member aperture 66 as best shown in FIGS. 2A, 2B, 4, 6 and 7A-7F.

Figure 3B:
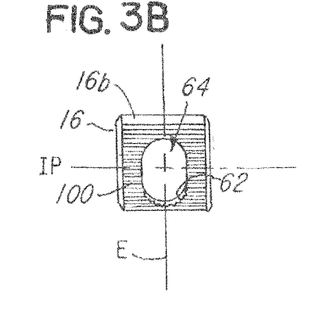
FIG. 3B is a fragmentary view of an end of the housing, showing teeth or serrations.
Figure 4:
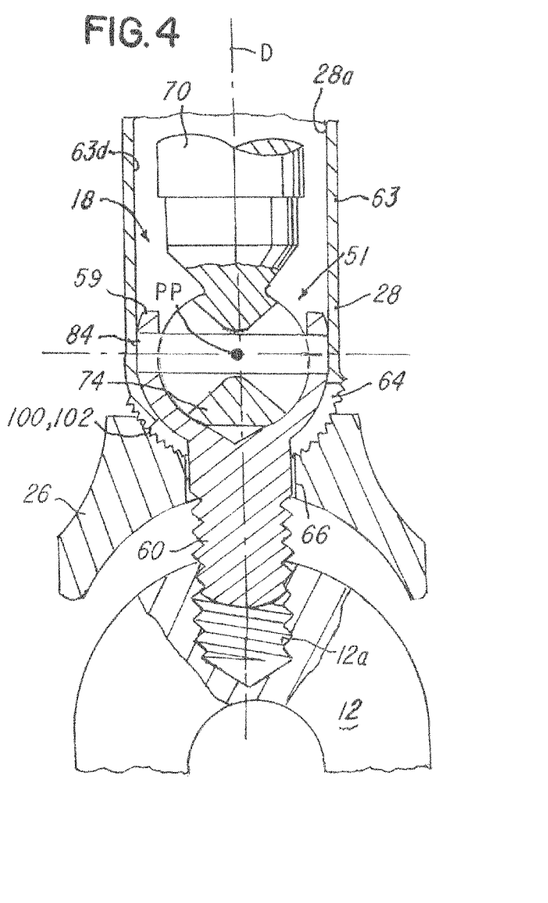
FIG. 4 is a fragmentary sectional view showing various details of a universal joint used in the embodiments shown in FIGS. 1-3B.
Figure 7A:
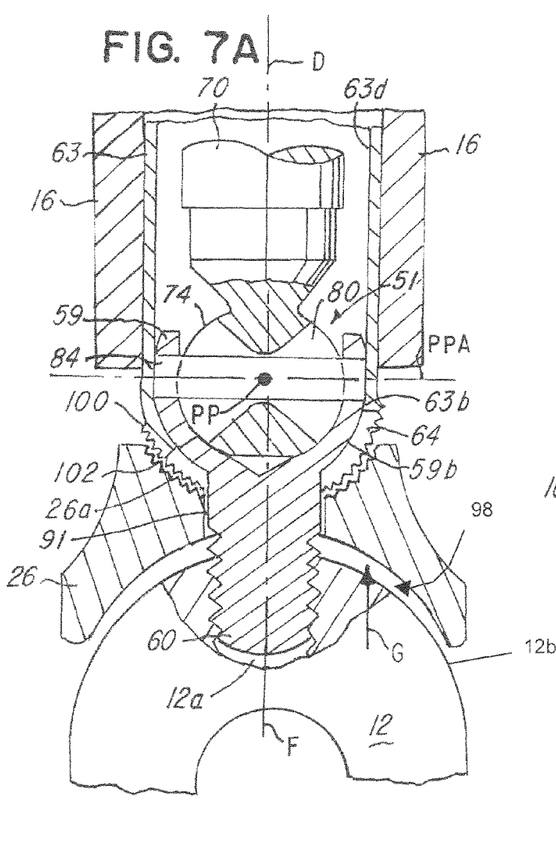
FIGS. 7A-7F are various sectional and fragmentary views that cooperate to show a pivotable movement of an implant holder and then a fixing, clamping or securing and locking of the implant to the implant holder after it has been pivoted and further showing the implant being clamped, fixed, locked or fastened in a pivoted position.
Figure 7B:
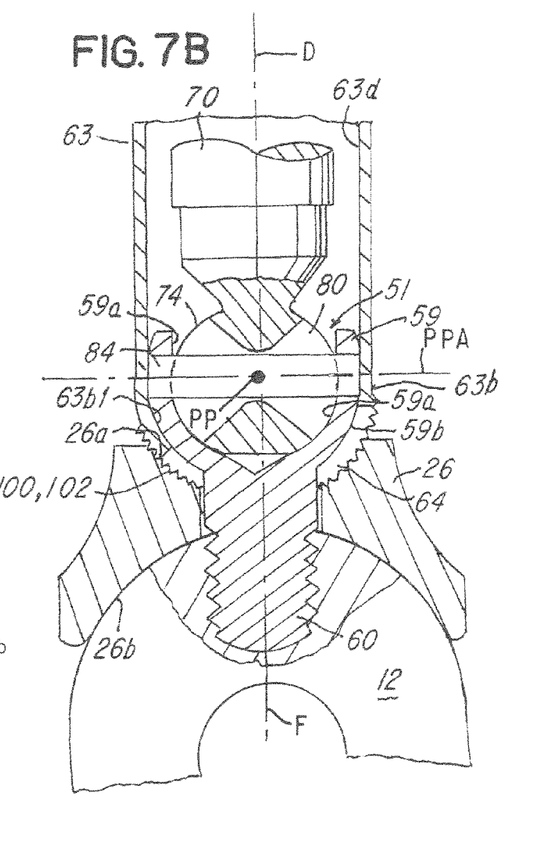

In the illustration being described and as best illustrated in FIG. 3B, notice that the slot 64 is asymmetrical about an imaginary plane IP that is generally transverse to a longitudinal axis D (FIG. 4) of the universal joint housing 63 and in a direction that is generally perpendicular to the direction to the axis E (FIG. 3B) of the slot 64. This enables and facilitates pivotal movement of the abutment member 26, threaded projection 60 and implant 12 in a first direction to a maximum first angle θ and a second direction to a maximum second angle φ, as illustrated in FIGS. 7C, 7E and 7D, 7F, respectively. Note that in one embodiment, the first angle θ is less than the second angle φ (as viewed in FIG. A), which permits lesser pivotal movement in the first direction compared to the second direction. Notice that the slot 64 permits nearly ninety degrees (90°) of pivotal movement of the threaded projection 60 in an arc or projection of a circle to the angle φ. In one embodiment, the angles θ and φ range from about 20 degrees to about 90 degrees, respectively, as shown in FIGS. 7E and 7F. In another embodiment, the range could be zero degrees to 90 degrees. In the later embodiment, the left side of slot 64 (as viewed in FIGS. 7A-7E) would be shortened so that surface 61 of the threaded projection 60 would abut the end of slot 64 and extend straight down as viewed in the FIG. 7H.

Figure 7C:
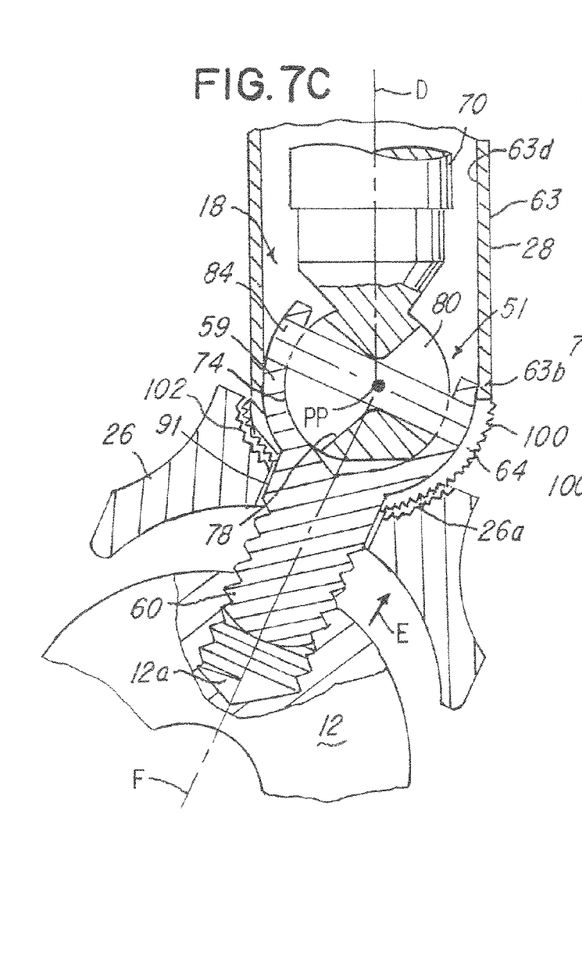
Figure 7D:
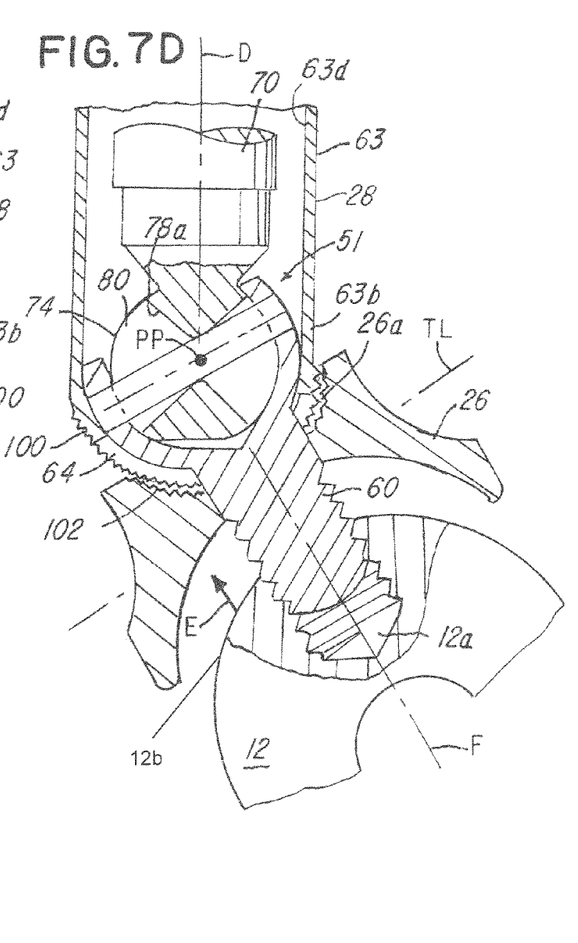
Figures 7E, 7F, 8A, 8B:
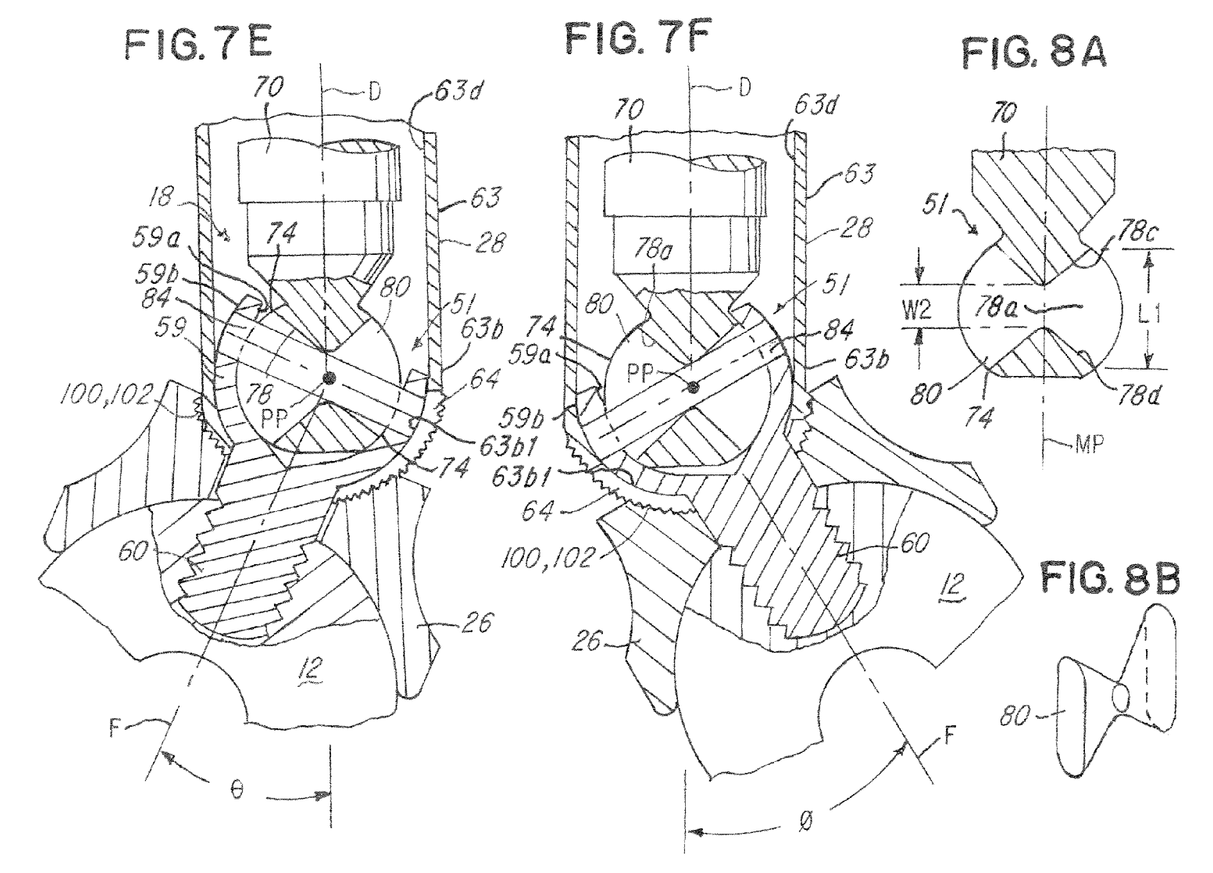
FIG. 8A is a fragmentary sectional view of a ball of the universal joint showing a butterfly or bow tie channel or aperture in one embodiment of the invention.
FIG. 8B is a view diagrammatically illustrating or outlining the butterfly or bow tie channel or aperture in the ball of the universal joint.

As previously mentioned, the surgical instrument 10 comprises the joint or universal joint 51 that operatively couples the drive member, rotatable member or rod 20 and the implant holder 58 to permit and enable rotational movement of the implant holder 58 before, during and after the abutment member 26 or threaded projection 60 is pivoted or moved, for example, from a home position (such as the exemplary position illustrated in FIG. 7A) to a pivoted or desired position (such as the exemplary position illustrated in FIGS. 7C and 7F). The threaded projection 60 has a threaded projection axis F (FIGS. 7C-7D) that is generally coaxial with the drive member or rotatable member axis D (FIG. 4) when in the home position, but when it is in the pivoted position, the axis F is not coaxial with the axis D (as illustrated in FIGS. 7C and 7D).

Figure 9A:
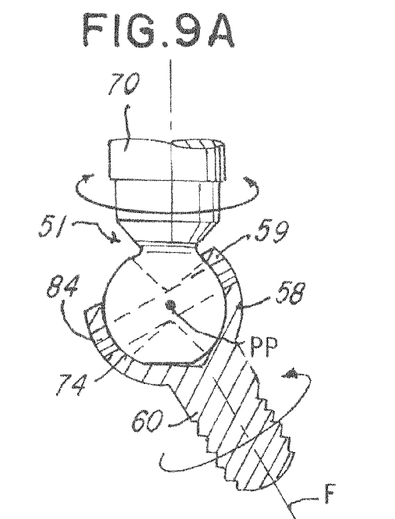
FIGS. 9A-9D are fragmentary sectional views illustrating a rotatable movement of a fastener or threaded projection during a pivot of a threaded projection, thereof.
Figure 9B:
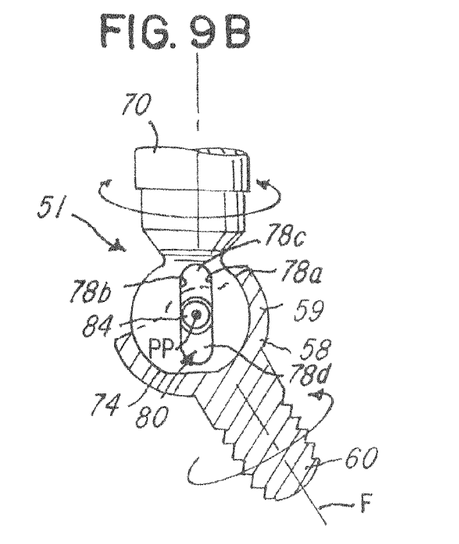
Figure 9C:
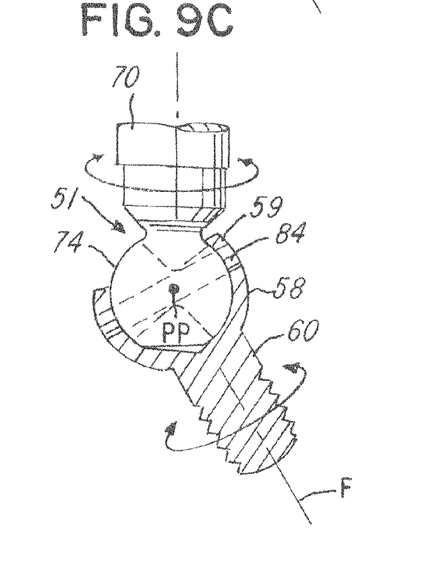
Figure 9D:
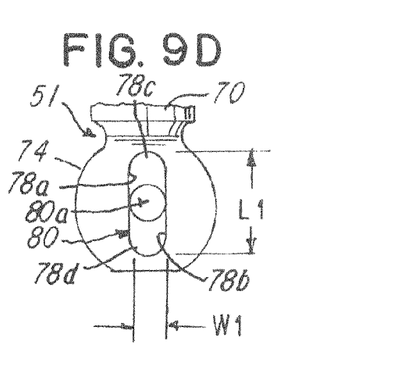

Notice that the ball support 70 of the universal joint 51 is coupled or fixed to an end 20b of the drive member, rotatable member or rod 20. In one embodiment, the joint or universal joint 51 comprises the ball 74 and a generally mating socket 59. The socket 59 is integral or monolithic with the threaded projection 60 and defines a head thereof. The ball 74 comprises a first internal wall 78a (FIG. 9B), a generally opposing second wall 78b and connecting walls 78c and 78d that cooperate to define a butterfly or bow tie aperture or slot 80 as best illustrated in FIGS. 7A-7F, 8A and 8B. The butterfly or bow tie aperture or slot 80 may be machined, milled and/or drilled into the ball 74. In the illustration being described and as best shown in FIG. 9D, note that a width W1 of the butterfly aperture or slot 80 is substantially smaller than a length L1 (FIG. 8A) of the butterfly or bow tie aperture or slot 80.

FIG. 8B is a view showing an outline of the butterfly or bow tie aperture or slot 80 in the ball 74. Notice that the butterfly or bow tie aperture or slot 80 extends completely through the ball 74 as shown in FIG. 8 and is generally circular in cross section at is midway point and defines a midway aperture 80a (FIG. 9D). A pivot pin 84 pivotally couples the socket head 59 to the ball 74 as shown in FIGS. 7A-7F and 9A-9D. A circumference or dimension of the midway aperture 80a approximately midway through the butterfly aperture or slot 80 is smaller than a circumference of the pivot pin 84. Thus, the midway aperture 80a circumferential dimension is slightly larger than a circumference of the pivot pin 84 to facilitate pivoting movement of the socket or head 59 with respect to the ball 74.

Returning to FIGS. 4-6 and as mentioned earlier, the head or socket 59 of the implant holder 58 is pivotally coupled to the ball 74 with the pivot pin 84 that is received in the butterfly aperture or slot 80. It is important to note that the pivot pin 84 is not coupled to the housing 16, but rather, couples the ball 74, which is at the end 70c of the ball support 70, to the head or socket 59 of implant holder 58. As will be described in more detail later herein, a user rotates the grip 22 which causes rotation of the drive member, rotatable member, or rod 20. The ball 74 rotation causes the walls 78a (FIGS. 9B and 9D) and 78b to drive and apply rotation torque or rotational movement to the pivot pin 84 which, in turn, causes the head or socket 59 of the implant holder 58 and threaded projection 60 to rotate. The threaded projection 60 rotation enables the user to screw and unscrew the threaded projection 60 into a threaded aperture 12a of the implant 12 to fix or secure the implant 12 to the instrument. It is important to understand that this rotation can occur before, during and after the threaded projection 60 or implant 12 has been pivoted to the pivoted or desired position as permitted by the universal joint 51.

Advantageously, the walls 78a and 78b that cooperate to define the butterfly aperture or slot 80 cooperate with the pivot pin 84 to substantially simultaneously enable and permit pivotal and rotational movement of the implant holder 58 and the threaded projection 60 by enabling the pivot pin 84 to pivot in the butterfly aperture or slot 80 in response to a pivotal movement of the implant 12, threaded projection 60 or the abutment member 26. The joint or universal joint 51 is adapted to also permit rotation of the implant holder 58 and threaded projection 60 before, during and after such pivoting.

Thus, the joint or universal joint 51 is adapted to permit a loosening of the implant 12 on the implant holder 58 so that the implant holder 58 may be pivoted or moved to a desired position (for example, from the position shown in FIG. 1A to the position shown in FIG. 1B) and also being responsive to rotational movement of the drive member, rotatable member or rod 20 to cause the threaded projection 60 to be screwed and tightened into the implant 12 so that it can become clamped, fixed or locked to the implant holder 58 after the implant holder 58 has been moved or pivoted to the desired or pivoted position. Further details of the joint or universal joint 51 and the pivotal movement and locking will now be described relative to FIGS. 4-7F.

Figure 6:
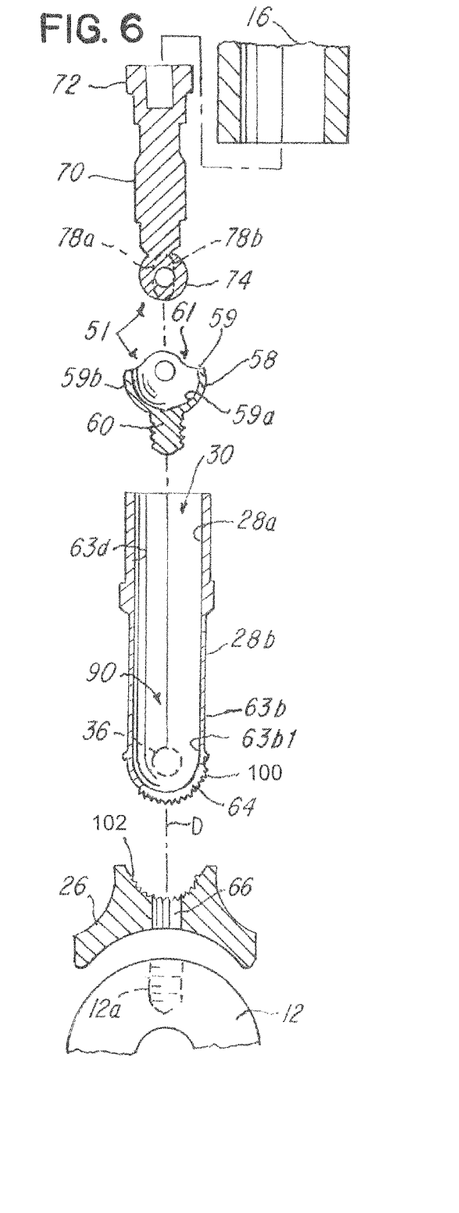
FIG. 6 is an exploded sectional view showing various details of the universal joint housing and abutment member illustrated in FIG. 5.

As illustrated in FIGS. 4-7F, the implant holder 58 comprises the threaded projection 60 which, when assembled into the universal joint housing 63, passes through the slot 64 (FIG. 3B) and through the aperture 66 of the abutment member 26. The head or socket 59 of the implant holder 58 receives and is secured to the ball 74 with pivot pin 84 as mentioned earlier. The head or socket 59 of the implant holder 58 comprises a generally spherical inner wall 59a and a generally spherical outer wall 59b as best illustrated in FIGS. 5 and 6. The end 63b of the universal joint housing 63 comprises a generally spherical inner wall 63b1 (FIG. 6) that defines a generally spherical seat area 90 (FIG. 6) that receives the head or socket 59 of the implant holder 58 such that the generally spherical outer wall 59b of the implant holder 58 becomes seated against or operatively associated with the generally spherical inner wall 63b1. In this regard, a shape of the generally spherical outer wall 59b generally complements the generally spherical shape of the spherical inner wall 63b1 to permit smooth and uninterrupted rotation movement of the implant holder 58 about its axis, as well as pivotal and rotational movement of the threaded projection 60 in the slot 64.

The ball 74 is also generally spherical as shown and is received in a seat 91 (FIG. 6) defined by the generally spherical inner wall 59a of the head or socket 59.

The head or socket 59 comprises a pair of generally cylindrical inner walls 86 (FIG. 5) and 88 that define apertures 92 and 94, respectively. After the ball 74 is received in the seat 91 defined by the generally spherical outer wall 59b, the pivot pin 84 may be placed into the butterfly aperture or slot 80 (FIG. 9) and in apertures 92 and 94 to pivotally and rotationally couple the implant holder 58 to the ball 74. In the illustration being described, the apertures 92 and 94 are sized to enable the pivot pin 84 to be press-fit therein. Alternatively, the pivot pin 84 may also be spot welded or secured in place by other means, such as an adhesive. As mentioned earlier herein, it is important to note that the pivot pin 84 does not extend axially into any wall of either the universal joint housing 63 or the housing 16 so that the head or socket 59 of the implant holder 58 may freely rotate and pivot within the spherical inner wall 63b1 of the universal joint housing 63 to enable the threaded projection 60 to be pivoted, screwed into, unscrewed or loosened and tightened into the implant 12.

The end assembly 31 is assembled as described, with the universal joint 51 being situated in the universal joint housing 63, with the threaded projection 60 extending through the slot 64 of end 63b and through aperture 66 in the abutment member 26. The ball support 70 is fixed to the drive member, rotation member or rod 20, which is also secured to grip 22, inside housing 16. The end assembly 31 is then inserted and fixed, such as be a press-fit, weld, adhesive or the like, into end 16b of housing 16.

As illustrated in FIGS. 7A-7F, the implant 12 comprises the implant female threaded aperture 12a that threadably receives the threaded projection 60 of the implant holder 58. In one embodiment, the abutment member 26 comprises a generally arcuate surface 26a that complements a shape of an outer implant surface 12b of the implant 12 and defines a seat area 98 (FIG. 7A) for receiving the arcuately-shaped implant surface 12b of the implant 12 as shown. The second end 63b of the universal joint housing 63 becomes associated with the end 16b of housing 16 and comprises a plurality of serrations or teeth 100 (FIG. 3A) that mate with a plurality of serrations or teeth 102 (FIG. 2) on the abutment member 26 as shown. In the illustration being described, the teeth 100 (best illustrated in FIG. 3A) cooperate with the teeth 102 (best illustrated in FIG. 2) of the abutment member 26 to lock these components together and prevent pivotal movement of the implant 12 and the abutment member 26 relative to the end 16b of the housing 16 after the implant 12 is clamped, fixed or locked thereto as described herein.

FIGS. 7A and 7C illustrate the first position or home position mentioned earlier wherein the axis F of the threaded projection 60 is generally coaxial with the axis D of the drive member, rotatable member, or rod 20. When the user rotates the grip 22 in a screwing or clockwise direction relative to the end 16a of the housing 16, a simultaneous and corresponding rotational movement of the drive member 20 and ball 74 occurs which rotatably drives the pivot pin 84 and head or socket 59. In response, the implant holder 58 and the threaded projection 60 are rotated, thereby causing the threaded projection 60 to be screwed into the female threaded aperture 12a. Continued rotation or screwing causes the implant surface 12b (FIG. 7A) of implant 12 to move in the direction of arrow G (FIG. 7A) toward and engage surface 26a of abutment member 26 which is urged to move toward the second end 63b of the housing 16. As the threaded projection 60 is screwed further, it causes the ball 74 to move toward the implant 12 and tightened against the spherical inner wall 16b1 (FIG. 7B) of second end 16b until the head or socket 59 of the generally spherical outer wall 59b engages the inner spherical surface or wall 16b1 of the housing 16, and the teeth 100 engage teeth 102 to clamp, fix or lock the implant 12 in the abutment member 26 to the end 63b of housing 63.

Advantageously, the implant 12 and outer wall 59b of the head or socket 59 cooperate to define a clamp for clamping of the wall 59b of the head or socket 59, wall 63b1 of universal joint housing 63 and abutment member 26 together. As mentioned earlier, the teeth 102 on abutment member 26 engage teeth 100 on the second end 63b of universal joint housing 63 to rigidly lock and clamp the abutment member 26 to the second end 63b, thereby locking the implant 12 to the surgical instrument 10.

If it is desired to change a position or pivot the implant 12 or the abutment member 26 (for example, to the position shown in FIGS. 1B, 1D, 7C-7F), then the grip 22 is rotated in a counterclockwise direction which causes the threaded projection 60 to be unscrewed or loosened from the threaded aperture 12a at the implant surface 12b (FIG. 7A) of the implant 12. In this regard, note that the generally arcuate surface 26a of the abutment member 26 is adapted and dimensioned to hold the implant 12 generally stationary in the spherical seat area 90 when the threaded projection 60 is rotated either clockwise or counterclockwise. Although not shown, the generally arcuate surface 26a of the abutment member 26 may comprise serrations or be otherwise roughened to further facilitate preventing relative movement between the implant 12 and the abutment member 26 when the drive member, rotatable member or rod 20 is rotated.

FIGS. 1B, 1D and 7C-7F illustrate pivotal movement of the implant holder 58, threaded projection 60 and implant 12 which will now be described. Note in FIG. 7C that the implant holder 58 has been pivoted or moved the angle θ to its leftmost position (as viewed in the figure). As mentioned earlier herein, the slot 64 is not symmetrical about a centerline of the imaginary plane IP (FIG. 3B) so that the extent of the pivotal movement of the abutment member 26 through the angle θ, illustrated in FIG. 7C, is less than the movement to the angle φ because the ends of the slot 64 limit movement of the threaded projection 60 between the angles θ and φ. The butterfly aperture or slot 80 (FIGS. 8A and 8B) in the ball 74 of the joint or universal joint 51 permits the pivot pin 84 and implant holder 58 to pivot between the angles θ and φ to the desired or pivoted position. It should be understood that the relationship of the abutment member 26 about its axis A (FIG.

3A) is along a consistent arc relative to the end 16b of the housing 16, which is guaranteed or assured by the flanges 40 and 42 which couple the abutment member 26 to the pivot pins 36 and 38 (FIG. 3A). As mentioned earlier, in one preferred embodiment, the projection member 60 of the implant holder 58 can pivot a total of approximately 90 degrees in angle φ, but only about zero degrees for angle θ. In another embodiment, the range is approximately 90 degrees in angle φ, but only about 20 degrees in angle θ.

As illustrated in FIGS. 7A, 7C and 7D, there is some play in the longitudinal movement of the abutment member 26 relative to the second end 16b so that the teeth 102 on the abutment member 26 may by spaced from and ride or pass over the teeth 100 at the end 63b of the universal joint housing 63 when the threaded projection 60 is unscrewed or loosened from the implant 12. This facilitates or enables the angular or pivotal position of the abutment member 26 relative to the second end 63b to be changed relatively easily.

The head or socket 59 of the implant holder 58 is rotatable in 360 degrees about the axis F of the threaded projection 60. Note that a pivot point PP (FIG. 7C) of the pivot pin 84 lies generally at a center of the ball 74. The abutment member 26 has the abutment member pivot axis A (FIG. 3A) which generally lies in the same imaginary plane as the pivot point PP of ball 74. The alignment of the axis A in this imaginary plane facilitates enabling the axis F of the threaded projection 60 to remain generally perpendicular to an imaginary tangent line TL (FIG. 7D) during pivotal movement of the threaded projection 60 and the abutment member 26.

As illustrated in FIGS. 1B, 1D, 7D and 7F, the user, such as a surgeon, positions or pivots the implant 12 and the abutment member 26 in the desired pivoted or angled position after loosening or unscrewing of the threaded projection 60 in the implant 12 by rotating grip 22 in an unscrewing direction, which is a counterclockwise direction in the illustration. In this example, it is assumed that the implant 12 is pivoted to the right as shown in FIGS. 1B, 1D, 7D and 7F. Once the implant 12 is pivoted to the desired position, the user or surgeon rotatably drives the handle or grip 22 (FIG. 1) in a clockwise or screwing direction which rotatably drives the ball 74 of the joint or universal joint 51 and correspondingly causes rotation of the implant holder 58 and the threaded projection 60. This causes the threaded projection 60 to become screwed into the threaded aperture 12a of implant 12. As mentioned earlier, this screwing action causes the implant 12 to move or be urged or driven in the direction of arrow E (FIG. 7D) until the implant surface 12b engages the arcuate support surface 26a of the abutment member 26. The screwing also causes the abutment member 26 to be driven toward end 63b and the abutment member teeth 102 to be driven toward and mate with the teeth 100 on end 63b. Note that generally spherical outer surface 59b of head or socket 59 is responsively driven toward implant 12 until it clamps against the generally spherical inner wall 63b1 (FIG. 6), thereby causing a clamping, locking or fixing of the ball 74, head 59, end wall 63b, projection member 60 and implant 12 together. This also fixes the implant 12 in a locked position on the instrument 10.

It is important to note that the joint or universal joint 51 enables the drive member, rotatable member, or rod 20 to cause the implant 12 to become clamped, fixed or locked to the implant holder 58 by enabling the drive member, rotatable member, or rod 20 to rotatably drive the universal joint 51, ball 74, head or socket 59, implant holder 58 and pivotal threaded projection 60 through a pivot of the head or socket 59 and the threaded projection 60. FIGS. 9A-9C, which are shown and illustrated without the housing 16 and abutment member 26 for ease of description and illustration, show this feature. For example, when the threaded projection 60 of implant holder 58 is in the angled, pivoted or moved to the desired position, such as the position shown in FIG. 9A, the threaded projection 60 may be rotated while into the pivoted or desired position by rotating the handle or grip 22. The drive member, rotatable member, or rod 20 may be rotated by rotating the handle or grip 22 to correspondingly rotate the ball 74 and socket 59, thereby causing a rotation in the threaded projection 60 about its axis F.

FIG. 9B illustrates a cross-sectional view of the universal joint 51 after the implant holder 58 and the threaded projection 60 have been rotated either 90 degrees or 270 degrees from the position shown in FIG. 9A (which would cause the pivot pin 84 axis PPA to project or extend perpendicular to the drawing sheet). FIG. 9C illustrates a further rotation of the implant holder 58 and threaded projection 60 to a position that is 180 or 360 degrees of rotation relative to the position shown in FIG. 9A.

Advantageously, a feature of the embodiments being described is that the joint or universal joint 51 is adapted to permit both pivotal and rotational movement of the implant holder 58 and the threaded projection 60 using a single connector drive member, rotatable member or rod 20. The cooperation of the components, namely the universal joint 51, ball 74, implant holder 58, housing 16 and abutment member 26 enable the loosing of the implant holder 58 so that the implant 12 can be pivoted or moved and then tightening of the implant 12 to cause the components to be clamped, fixed or locked together using a single drive member assembly. The pivotal and rotational movement is achieved using the single drive member, rotatable member or rod 20 having the universal joint 51, which has been found to improve that performance of the instrument 10 while reducing its complexity.

Although the illustration being described shows a ball 74 and head or socket 59, it does not have to be a strict ball and socket configuration and the components 74 and 59 could have other configurations provided that they permit and allow the pivotal and rotational movement as described herein.

Advantageously, the implant holder 58 shown and described permits the use of standard cages. In other words, a custom cage having a custom joint is not required. The cage size can change as well. This is permitted because the pivot point is located in the holder, not the cage. This feature also results in the graft area in the implant 12 to be maintained and not reduced as was the case with some prior art devices.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A surgical instrument for inserting an implant, the surgical instrument comprising:
   a housing having a longitudinal axis, a proximal end and a distal end, said housing having a through slot extending through said distal end of said housing;
   a rotatable member rotatably positioned in said housing, said rotatable member having an elongated member extending between said proximal end and said distal end of said housing and comprising a grip generally located at said proximal end of said housing;
   an implant holder connected to said elongated member of said rotatable member, said implant holder having a spherical or rounded head having a spherical or rounded external surface that mates with or engages a spherical or rounded internal wall surface of said housing at said distal end and a securing member comprising a threaded projection monolithic with said spherical or rounded head, said threaded projection extends through said through slot in said distal end of said housing and is configured to engage with and hold said implant;

a universal joint coupling said implant holder to said elongated member; said universal joint situated in said housing between said grip and said threaded projection, said universal joint allowing said implant holder to be rotatably driven about a longitudinal axis of said implant holder when said threaded projection is in a pivoted position at which said axis of said implant holder is not coaxial with said longitudinal axis of said housing;

wherein said universal joint comprises a ball and socket joint that is rotatable within said distal end of said housing, said ball and socket joint comprising:

a spherical or rounded socket defined within said spherical or rounded head of said implant holder; a distal end of said elongated member having a ball that is received in said spherical or rounded socket, said ball having at least one through aperture extending therethrough;

at least one pivot pin having a pivot in axis extending through said at least one through aperture of said ball; said at least one pivot pin pivotally coupling said ball in said spherical or rounded socket of said implant holder, such that said pivot in axis of said at least one pivot in is not coaxial with said longitudinal axis of said housing when the ball is coupled in said socket and said threaded projection is in said pivoted position;

said pivot pin rotatably driving said spherical or rounded socket about said longitudinal axis of said implant holder in response to rotation of said rotatable member about an axis of said elongated member being coaxial with said longitudinal axis of said housing and permitting said implant holder to pivot relative to said ball about said pivot pin axis of said at least one pivot pin, so that said securing member pivots to said pivoted position at which said axis of said implant holder is not coaxial with said longitudinal axis of said housing; and an abutment member pivotally and adjustably coupled to said housing, said abutment member being external to said distal end of said housing, said abutment member comprising:

an abutment member first surface matingly connected or engaged to an external surface of said distal end of said housing when said implant is in a clamped, fixed or locked position with said housing, an abutment member second surface against which said implant configured to be driven in order to clamp, fix or lock said implant into a clamped, fixed or locked position relative to said housing, an abutment member through aperture extending through said abutment member first and second surfaces through which said threaded projection extends, said abutment member being pivotally adjustable relative to said distal end of said housing and being adapted to be clamped, fixed or locked to said distal end of said housing while in said pivoted position in response to said threaded projection being rotatably and threadably received in a threaded opening in said implant which causes said implant to be driven against said abutment surface and causes abutment member first surface to engage said distal end of said housing;

wherein said abutment member first surface and said distal end of said housing have a plurality of teeth or serrations that matingly engage or matingly connect with one another to prevent further pivotal movement of said abutment member and said implant relative to the housing when said abutment member is coupled, fixed or locked to said distal end of the housing;

wherein said abutment member further comprises a plurality of flanges for pivotally coupling said abutment member to said housing so that said abutment member can pivot relative to said distal end of said housing, a connection for coupling said plurality of flanges and said distal end of said housing together, said connection comprising at least one pin or projection having an axis and at least one opening configured to receive said at least one pin or projection so as to couple a first end of said plurality of flanges of said abutment member to said distal end of said housing; wherein at least one of said distal end of said housing or said first end of at least one of said plurality of flanges includes the at least one pin or projection and the other includes the at least one opening, said connection permitting said abutment member to move longitudinally relative to said axis of said implant holder towards said distal end of said housing when said threaded projection is secured into said implant and permitting said abutment member to pivot about the axis of the at least one pin or projection of said connection, thereby enabling said abutment member to be releasably and adjustably secured to said distal end of said housing.

2. The surgical instrument as recited in claim 1 wherein said abutment member first and second surfaces are generally arcuate.

3. The surgical instrument as recited in claim 2 wherein said implant comprises an implant surface that is generally arcuate, said implant surface complementing and mating with said abutment member second surface when said implant is clamped, fixed or locked onto the surgical instrument.

4. The surgical instrument as recited in claim 2 wherein said abutment member second surface comprises abutment member teeth or serrations to facilitate clamping, fixing or locking said implant to the surgical instrument.

5. The surgical instrument as recited in claim 4 wherein said implant comprises implant teeth or serrations that mate with said abutment member second surface teeth or serrations.

6. The surgical instrument as recited in claim 1 wherein said at least one through aperture in said ball is a butterfly through aperture extending through said ball, said butterfly through aperture being adapted to receive said pivot pin and to permit said socket to pivot about said pivot pin as and to be rotatable driven by said pivot pin.

7. The surgical instrument as recited in claim 1 wherein said pivot pin axis of said pivot pin is generally perpendicular to said longitudinal axis of said elongated member.

8. The surgical instrument as recited in claim 7 wherein said pivot pin axis and said longitudinal axis of said rotatable member intersect.

9. The surgical instrument as recited in claim 1 wherein said universal joint is adapted to permit both a loosening of said implant on said implant holder so that a position of said implant on the surgical instrument may be adjusted or moved to said pivoted position and a rotation of said securing member to cause said implant to be clamped, fixed or locked onto the surgical instrument.

10. The surgical instrument as recited in claim 4 wherein the surgical instrument further comprises said implant.

* * * * *